US006368267B1

(12) United States Patent
Lenhardt

(10) Patent No.: US 6,368,267 B1
(45) Date of Patent: Apr. 9, 2002

(54) STAPEDIAL-SACCULAR STRUT AND METHOD

(75) Inventor: Martin L. Lenhardt, Hayes, VA (US)

(73) Assignee: Sound Techniques Systems, LLC, Arlington, VA (US)

( * ) Notice: Subject to any disclaimer, the term of this patent is extended or adjusted under 35 U.S.C. 154(b) by 0 days.

(21) Appl. No.: 09/418,990

(22) Filed: Oct. 14, 1999

Related U.S. Application Data

(60) Provisional application No. 60/104,232, filed on Oct. 14, 1998.

(51) Int. Cl.[7] ............................................... H04R 25/00
(52) U.S. Cl. ....................................................... 600/25
(58) Field of Search ........................ 600/25; 607/55–57

(56) References Cited

U.S. PATENT DOCUMENTS

| 4,982,434 A | | 1/1991 | Lenhardt et al. ............ 381/68.3 |
| 5,318,502 A | * | 6/1994 | Gilman ........................ 600/25 |
| 5,344,387 A | * | 9/1994 | Lupin ............................ 600/25 |
| 5,498,226 A | * | 3/1996 | Lenkauskas ................. 600/25 |
| 5,531,787 A | * | 7/1996 | Lesinski et al. ........... 600/25 X |
| 5,782,744 A | * | 7/1998 | Money ........................ 600/25 |

FOREIGN PATENT DOCUMENTS

| WO | WO90/09152 | 8/1990 |
| WO | EP0518236 A1 | 12/1992 |
| WO | WO98/06236 | 2/1998 |

* cited by examiner

Primary Examiner—John P. Lacyk
Assistant Examiner—Joseph A Cadugan
(74) Attorney, Agent, or Firm—Foley & Lardner

(57) ABSTRACT

A system and method for an auditory inner ear prosthesis. A strut connects the medial surface of the stape footplate with the wall of the saccule. The strut spans the 1.5 mm vestibule between the saccule and the stapes. The strut is a synthetic elastic connector constructed of biocompatible material such as sylastic. The strut converts eardrum or ossicle vibration into saccular stimulation. The saccule is a large otic receptor organ capable of coding sound, and plays a role in reptilian hearing. For human ears, the saccule is so isolated from the eardrum and related elements that sound stimulation is ineffective. The strut allows for better stimulation by direct coupling. In cases of deafness, the saccule can serve as an alternative ear.

16 Claims, 10 Drawing Sheets

RESULTS OF MEASUREMENTS IN NORMAL TEMPORAL BONES

| PLANES | MEASURING POINTS | UTRICLE | | | | | SACCULE | | | |
|---|---|---|---|---|---|---|---|---|---|---|
| | | n | MIN | MAX | MEAN | SD | n | MIN | MAX | MEAN | SD |
| SUPERIOR | P | 10 | 0.62 | 2.10 | 1.30 | 0.48 | 10 | 1.19 | 1.76 | 1.51 | 0.19 |
| 0.2 mm SUPEROCENTRAL | PC | 9 | 0.58 | 2.00 | 1.56 | 0.44 | 9 | 2.19 | 3.10 | 2.52 | 0.29 |
| | C | 9 | 1.31 | 2.62 | 1.91 | 0.40 | 9 | 1.66 | 2.29 | 1.96 | 0.20 |
| | AC | 9 | 1.47 | 2.71 | 2.00 | 0.39 | 9 | 1.61 | 2.14 | 1.82 | 0.18 |
| | A | 9 | 1.54 | 2.81 | 2.11 | 0.38 | 9 | 1.56 | 1.95 | 1.73 | 0.14 |
| CENTRAL | | 9 | 2.05 | 3.43 | 2.72 | 0.40 | 9 | 0.76 | 1.50 | 1.27 | 0.21 |
| | P | 10 | 1.29 | 2.16 | 1.70 | 0.28 | 10 | 2.29 | 3.05 | 2.66 | 0.22 |
| | PC | 10 | 1.59 | 2.81 | 2.06 | 0.37 | 10 | 1.70 | 2.24 | 2.03 | 0.16 |
| | C | 10 | 1.68 | 2.95 | 2.15 | 0.39 | 10 | 1.63 | 2.16 | 1.93 | 0.15 |
| | AC | 10 | 1.77 | 3.10 | 2.25 | 0.40 | 10 | 1.61 | 2.05 | 1.82 | 0.14 |
| | A | 10 | 2.38 | 3.57 | 2.82 | 0.41 | 10 | 0.86 | 1.68 | 1.32 | 0.24 |
| 0.2 mm INFEROCENTRAL | P | 10 | 1.38 | 2.43 | 1.77 | 0.34 | 10 | 2.18 | 2.95 | 2.59 | 0.26 |
| | PC | 10 | 1.54 | 3.00 | 2.08 | 0.47 | 10 | 1.93 | 2.30 | 2.13 | 0.14 |
| | C | 10 | 1.61 | 31.4 | 2.19 | 0.47 | 10 | 1.82 | 2.19 | 2.03 | 0.15 |
| | AC | 10 | 1.73 | 3.24 | 2.29 | 0.48 | 10 | 1.73 | 2.10 | 1.92 | 0.14 |
| | A | 10 | 2.14 | 4.05 | 2.88 | 0.58 | 10 | 1.00 | 1.86 | 1.50 | 0.30 |
| INFERIOR | | 10 | 1.67 | 2.95 | 2.20 | 0.39 | 10 | 2.05 | 2.71 | 2.40 | 0.18 |

FIG. 8B

MEASUREMENTS ARE IN MILLIMETERS AND SHOW DISTANCES TO UTRICLE AND SACCULE FROM POINTS ON MEDIAL SURFACE OF STAPES FOOTPLATE. P-POSTER BORDER, PC-0.2mm POSTERIOR TO MIDDLE, C-MIDWAY, AC-0.2mm ANTERIOR TO MIDDLE, A-ANTERIOR BORDER.

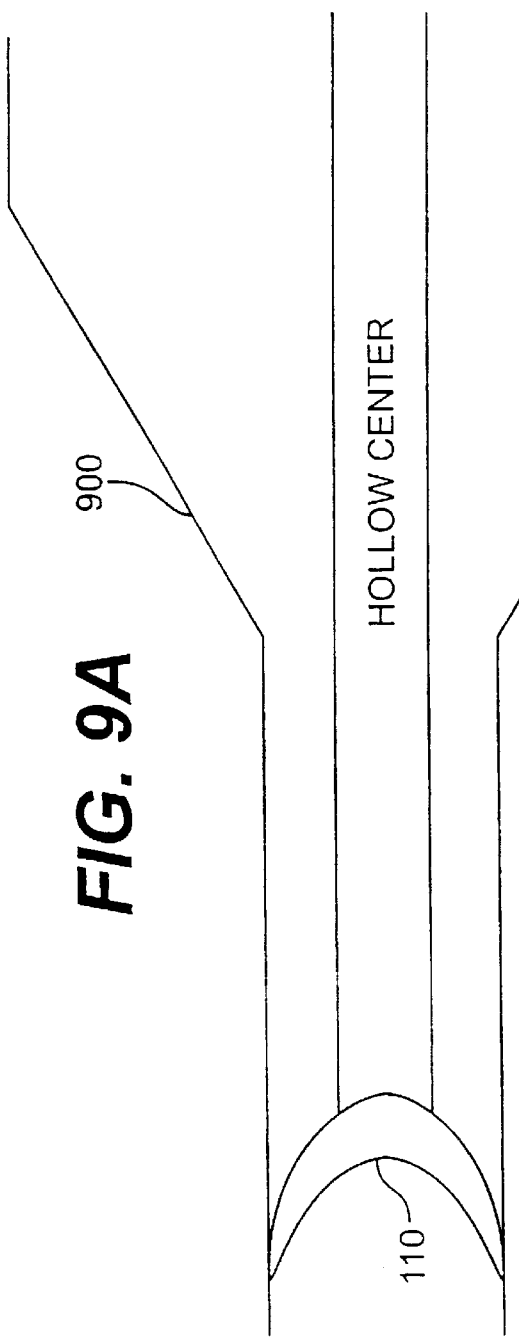
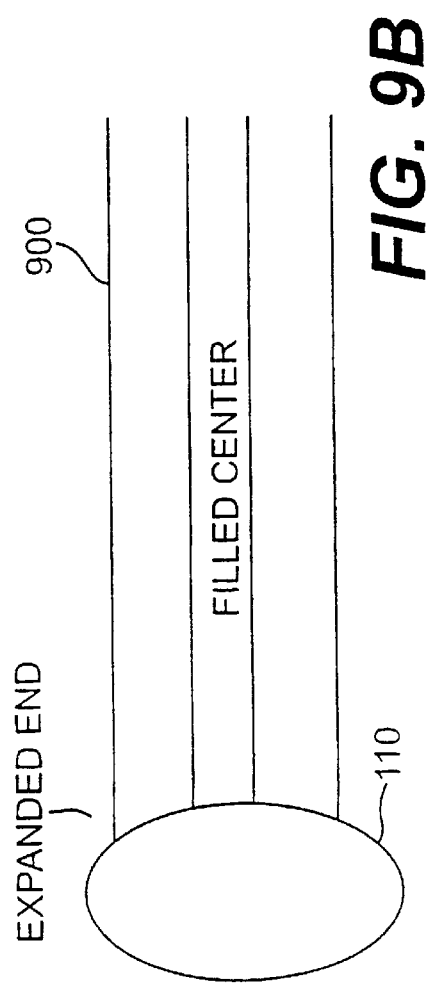

STAPEDIAL-SACCULAR STRUT AND METHOD

This application claims priority of U.S. Provisional Application No. 60/104,232 filed in the United States Patent and Trademark Office on Oct. 14, 1998, the entirety of which is incorporated by reference.

BACKGROUND OF THE INVENTION

1. Field of the Invention

The present invention relates to a system and method for an auditory ear prosthesis. In particular, the present invention relates to the construction of a strut for connecting the medial surface of the stape footplate with the wall of the saccule.

2. Description of the Related Art

One type of conventional hearing aid provides for an air-conduction amplifying system such that a microphone picks up air conduction sounds, amplifies them and presents them in the ear canals as an air conduction signal to the eardrum. Such hearing aids offer a small frequency range as well as a small dynamic range of intensity.

Another type of conventional hearing aid is called a bone conduction hearing aid, which has been developed for users where the conventional air-conduction hearing aid is not satisfactory in improving hearing for those users. A bone conduction hearing aid is attached to the head of the user, and the output from a microphone pick-up is amplified and fed into a device which causes bone vibration. These devices operate over a small dynamic range and are designed principally for persons whose middle ears could not be surgically repaired or for very young children who have abnormalities of the middle ear that cannot be surgically repaired until they are older. As such, bone conduction hearing aids are rarely used.

Another type of conventional hearing aid involves implanting rare earth magnets in the temporal bone, and a microphone electronic coil system is used to cause the magnets to vibrate. The vibration of the magnets produces bone conduction hearing. These devices are also rarely used because of the surgery involved in drilling out the bone and installing the magnets therein.

Another type of hearing aid utilizes the supersonic frequency band, such as from 20,000 Hz and above, as disclosed in U.S. Pat. No. 4,982,434, which is incorporated in its entirety herein by reference. In such supersonic-frequency hearing aids, air conduction sounds in the audiometric range (from 100 Hz to about 10,000 Hz) are frequency-shifted to about 108 kHz or higher, and then these supersonic frequencies are transmitted by bone conduction or the like to the human sensory system. These signals are delivered by a bone conduction attachment, such as a high fidelity electrical to vibrator transducer, functionally connected for bone conduction in the head.

In U.S. Pat. No. 4,982,434, it was hypothesized that the supersonic hearing aid provides hearing to the user based on a system of hearing quite distinct from normal hearing based on air conduction. Instead, it uses bone conduction and parallels the primary hearing response of reptiles. In some reptiles, there is reduced air conduction hearing in reference to bone conduction. Hearing is mediated via both the cochlea and the saccule. In man, the saccule has been considered an organ responsible for balance and determining acceleration and movement. In reptiles, the saccule is a hearing instrument and it possesses hearing potential in amphibia and is the hearing organ of fish as well.

The evolution of the mammalian ear has spanned nearly 200 million years. Reptilian mammals responded to selective pressures and developed very sensitive air borne receivers with wide frequency ranges. The closest living relative to the common ancestor of these reptilian mammals are the extant turtles. While turtles hear a restricted range of frequencies, they preferentially process sound in the form of vibration. Turtles have at least two sensory receptors in their inner ears, the cochlea and the saccule. The cochlea is stimulated by bone conduction, which is different from the means of conduction in mammals. However, there also exists in turtles a physical connection between the wall of the saccule and the middle ear bone (stapes), with this physical connection not existing in mammals. Thus, when sound strikes the eardrum of a turtle, both the cochlea and the saccule are stimulated. In the case of a mammal, the saccule is isolated from direct contact with the stapes, and only very intense vibration of the stapes is translated to a corresponding vibration in the saccule.

The mammalian auditory system developed a sensitive receiver by evolving a thin, taught eardrum connected to a three-bone middle ear system that is capable of matching impedances between sound in air and vibration in inner ear fluid (perilymph). This ear development in sensitivity and in frequency range may have been detrimental to the saccule if it remained directly coupled to the middle ear. A very sensitive receiver may have exerted too much displacement on the saccule, hence overloading it. As such, it is hypothesized that the disarticulation of the saccule from the stapes may have been an adaptive mechanism for mammals.

The supersonic hearing aid as disclosed in U.S. Pat. No. 4,982,434 was believed to utilize direct bone transmission to the saccule, thereby enabling hearing to be maintained via a system independent of air conduction and the inner ear, although integrated with the air conduction system.

The supersonic hearing aid may not be suitable for every patient. Accordingly, there is a need to provide alternative approaches for saccule-mediated hearing.

SUMMARY OF THE INVENTION

It is an object of the present invention to provide a method and a system of inner ear activation through a prosthesis that connects the saccule to the stapes of a human ear.

The above-mentioned object and other advantages may be obtained by an auditory prosthesis system for a human inner ear that includes an eardrum, a saccule and a stapes. The system includes at least one strut that is disposed between the saccule and the stapes. Movement of the stapes is directed to the saccule by way of the at least one strut.

The above-mentioned object and other advantages also may be obtained by a method of implanting a hearing aid device into an inner ear of a human, the inner ear including a saccule and a stapes. The method includes a step of affixing one end of a strut to the stapes, wherein the strut has a hollow middle for receiving a material. The method also includes a step of applying the material into the hollow middle of the strut, thereby causing the other end of the strut to contact the saccule. Physical movement of the stapes caused by movement of an eardrum is directed to the saccule by way of the strut.

The above-mentioned object and other advantages also may be obtained by a method of implanting a prosthesis into an inner ear to enhance hearing. The method includes a step of providing a strut between a saccule and a stapes of the inner ear, thereby providing a direct contact between the saccule and the stapes. The strut provides direct stimulation of the saccule based on stimulation of the stapes.

BRIEF DESCRIPTION OF THE DRAWINGS

The above-mentioned object and advantages of the invention will become more fully apparent from the following detailed description when read in conjunction with the accompanying drawings, with like reference numerals indicating corresponding parts throughout, and wherein:

FIGS. 8A and 8B show detailed distance data between the stapes and the saccular wall, with that data being obtained from an article on the human ear; and FIGS. 9A and 9B show the structure of a sleeve used to form and position a strut according to the invention, in an unfilled and a filled state, respectively.

DETAILED DESCRIPTION OF THE PREFERRED EMBODIMENTS

Figure 1:
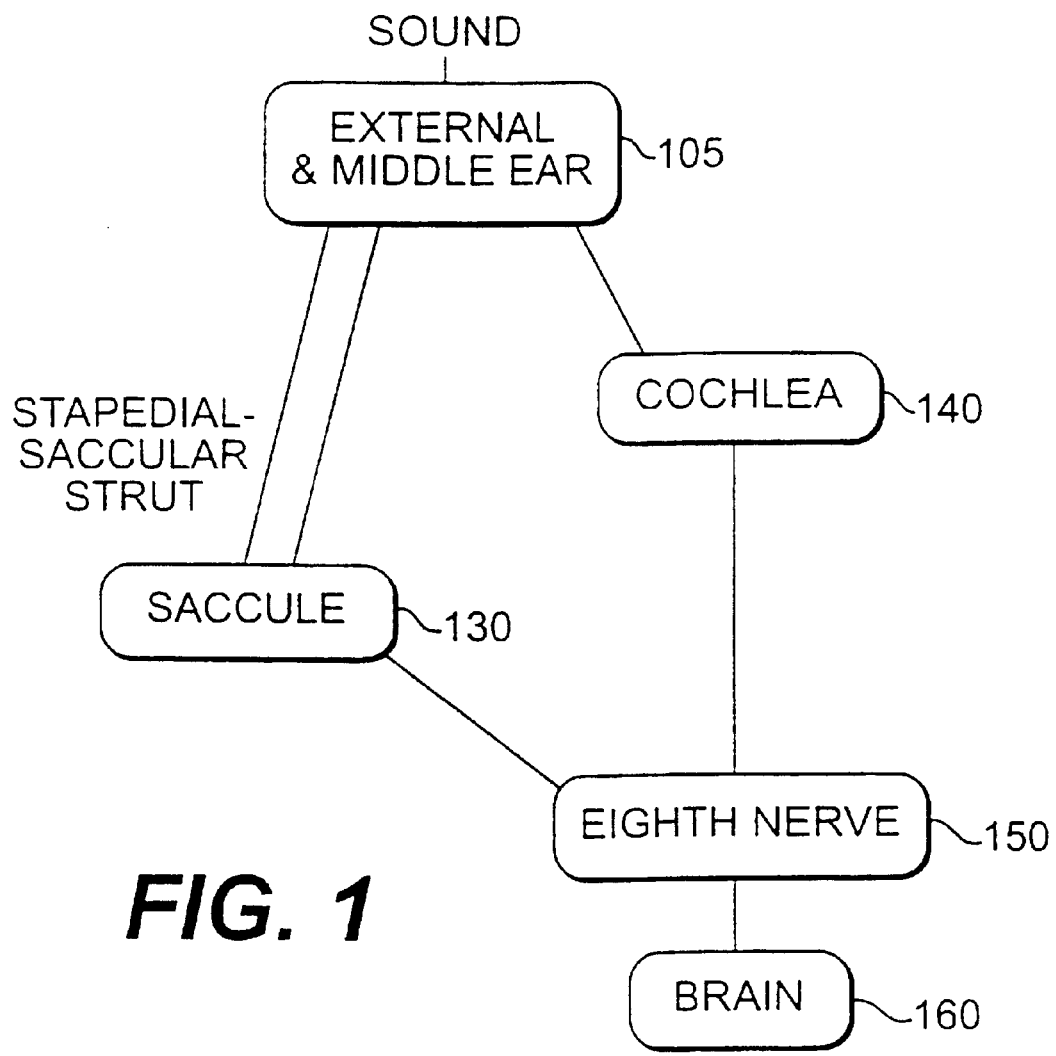
FIG. 1 is a block diagram of the flow of sound from the external ear sensed as pressure, converted to vibration by the inner ear stimulating the cochlea and the saccule through an implanted stapedial-saccular strut and converted to neural signals in the nerve and the brain.

The present invention is directed to a method and a system for an implanted auditory vestibular prosthesis, or stapedial-saccular strut, which functions as a coupler of middle ear vibration to the saccule of the vestibular system. The method and system provide additional stimulation to the saccule when external signals are applied to the ear by either air conduction and/or bone conduction. Speech recognition is boosted not only during natural conditions, but also with traditional air-conduction amplification techniques.

To date, it is not believed that there has been an inner ear implantable prosthesis developed to drive the saccule by the displacement of the middle ear system, until the present invention. Inner ear implants designed to electrically stimulate the cochlea, so-called cochlear implants, are intracochlear devices. Devices to stimulate the inner ear by stimulating the round window of the inner ear currently exist, but these are middle ear implants. Implantable hearing aids also exist, but these attach to the middle ear bones, including the stapes, but only within the middle ear space. These devices do not attach to the saccule.

The present invention relates to an auditory vestibular prosthesis and a method of making and implanting such a device. The prosthesis couples the middle ear bone (stapes) to the wall of the saccule, and thus corresponds to a stapedial-saccular strut. The strut is preferably a synthetic elastic connector to the saccule, and transmits stapedial displacements, which occur as a result of eardrum movements indicated by sound waves, as a vibration to the saccule.

In a first embodiment, a strut is formed using a "sleeve". The sleeve is hollow and contains a collapsed reservoir end that is distended by injection of a synthetic silicon through the sleeve. The sleeve is preferably formed of cured sylastic. The injected synthetic silicon eventually cures to achieve a solid form having a predetermined shape, to thereby form the strut or prothesis. The reservoir end of the sleeve expands due to the injection of fluid into the sleeve, and thereby allows a balloon end of the strut formed by way of the sleeve to make contact with the saccular wall and to adhere thereto. In a second embodiment, each strut is hollow (cylinder-shaped), without a collapsed reservoir end. In the second embodiment, a balloon-like formation at the distal end of the sleeve (the end nearest the saccule) is formed due to pushing each sleeve (with uncured sylastic liquid having been pumped into the hollow middle of the sleeve) in a direction towards the stapes. This pushing causes some of the liquid sylastic in the sleeve to seep out of the reservoir end of the sleeve, thereby forming a balloon-like shape at that end.

As explained in the Background section, it is hypothesized that the disarticulation of the saccule from the stapes may have been an evolutionary process for mammals. This may have been due to: a) excellent sensitivity of the human ear by air conduction, and b) wide frequency range of the human ear. In the case of a human experiencing some degree of hearing loss, these two factors are no longer present.

The embodiments of the present invention provide a coupling of the stapes to the saccule in cases of pronounced sensorineural hearing loss, in order to increase the number of sensory elements responding to sound. This may also increase speech reception and intelligibility. A block diagram of an embodiment of the present invention is given in FIG. 1. Sound enters the ear canal. The sound displaces the eardrum and middle ear bones 105, thereby stimulating the cochlea 140, which in turn provides corresponding signals to the eighth nerve 150, which in turn provides corresponding signals to the brain 160.

Figure 2:
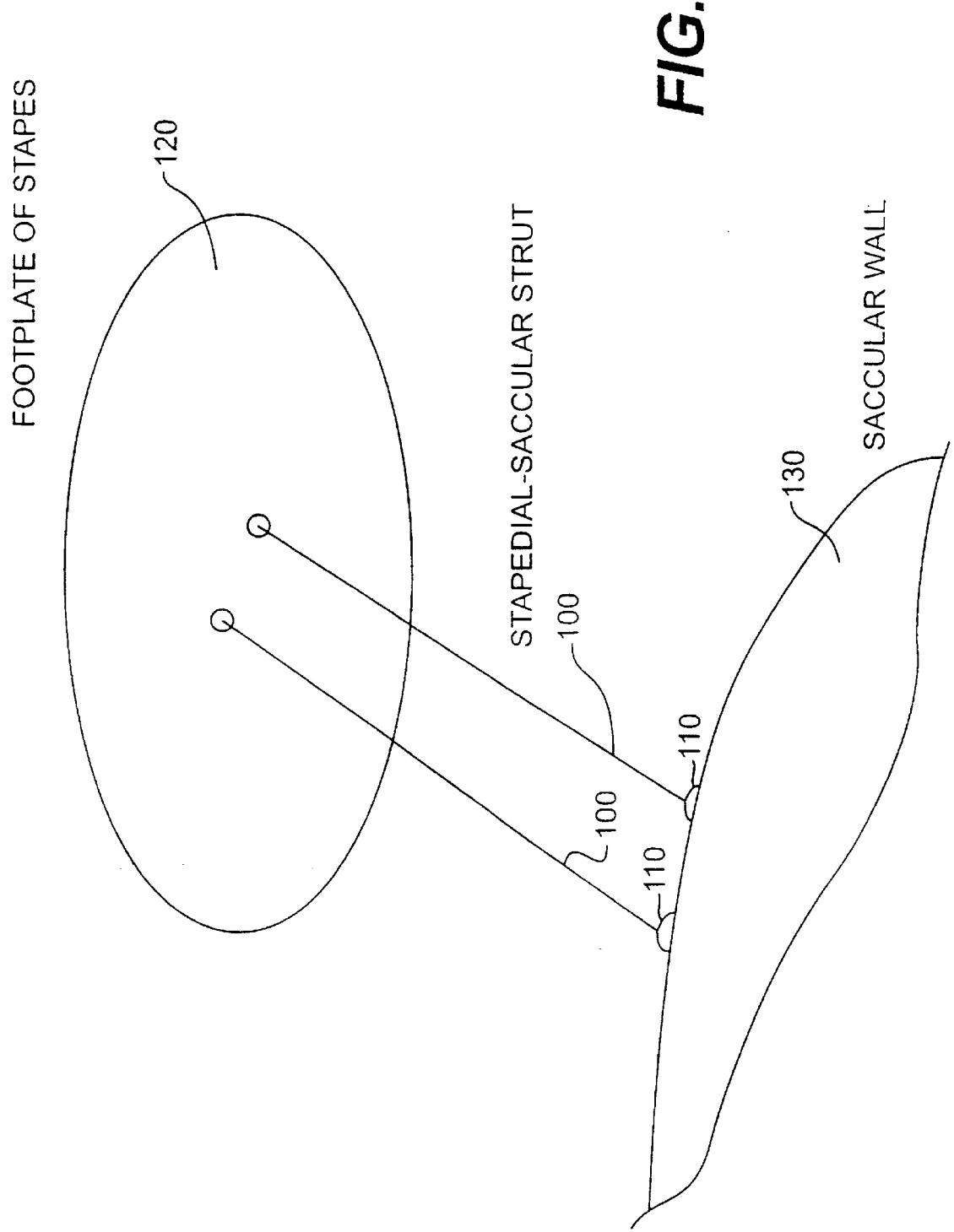
FIG. 2 is an enlarged block diagram of the saccule and the stapes interfacing with the stapedial-saccular struts according to the invention.

Referring now to FIGS. 1 and 2, in one embodiment of the present invention, at least one synthetic stapedial-saccular strut (SSS) 100 is disposed between the footplate of the stapes 120 and the saccular wall 130. By this connectivity, the saccule 130 is physically coupled (via the SSS 100) to the middle ear 105, resulting in the simultaneous stimulation of both endorgans (saccule 130 and cochlea 140) when sound moves the eardrum. The strut itself is formed into the inner ear using a sleeve having a cylindrical shape with a hollow middle. Sylastic in solid form is readily available in sheets, and a sheet can be fashioned into a tube, to thereby create the sleeve.

The stapedial-saccular struts 100 can be positioned by drilling a hole for each strut 100 near the center of the footplate 120, and then inserting each sleeve at a location close to the center of the footplate 120. Other approaches can be undertaken for positioning and attaching the strut to the footplate 120. Preferably, each sleeve is inserted a small amount into a hole drilled in the footplate 120.

Each sleeve 100 is preferably a small diameter (e.g., 0.02 mm) bioactive (or biocompatible) polymer. By way of example and not by way of limitation, each strut 100 is constructed of a biocompatible organic polymer, such as sylastic or a water swell hydrophilic gel, or the like. The actual length of the struts 100 depends on the physical characteristics of the particular ear in which the struts 100 are to be inserted. This length may be determined by a variety of ways, such as by taking a magnetic resonance image (MRI) of the patient's head, to thereby determine the distance between the stapes 120 and the saccule 130 for that patient. Once that distance is determine, properly-sized struts may be constructed, and then inserted into the appropriate position within the ear. The inserting of the sleeves that provide the "template" for the strut formation in the inner ear may be performed in any of a variety of ways, such as by using a hypodermic needle to implant the struts into the hollow middle portions of the sleeves.

In accordance with the first embodiment of the present invention, each sleeve (being formed from cured sylastic) has a small reservoir end that expands when the sleeve is filled with sylastic in liquid (uncured) form. Sylastic is biocompatible with the inner ear tissue, and is an ideal compound for providing a prosthesis in the ear. The expanded reservoir end will make contact with the saccular wall, and form a kind of fluid spring. In accordance with the second embodiment of the present invention, each sleeve is formed from cured sylastic into a hollow cylinder, and uncured, liquid sylastic is pumped into the hollow middle of the sleeve. The liquid sylastic is pumped into the sleeve after the sleeve has been inserted into a central position on the footplate of the stapes where a hole has been drilled. The sleeve is pulled back from the saccular wall to allow the liquid sylastic in the middle of the sleeve to balloon at the saccular wall end. This forms a strut having a balloon-like end, as the liquid sylastic cures in that particular shape. In the first embodiment, there is no need to pull the sleeve back, since the liquid sylastic is pumped into the sleeve at an amount enough to fill the reservoir end of the sleeve to a desired size.

As discussed above, multiple struts can be used to ensure adequate coupling between the stapes and the saccule. In each of the embodiments of the present invention, the perilymph that is displaced by the introduction of the strut is siphoned off, preferably through a tap in the stapes, and sealed after implantation of the stapes. That way, the ambient pressure of the inner ear is maintained. Perilymph is the inner ear fluid that is bridged by the strut, and when the strut is inserted into the ear, some of the perilymph must be siphoned off, or else the strut will displace the existing perilymph and it will bulge the oval window (where the stapes is situated) and the round window (which is located a few mm below the oval window). Preferably, the amount of fluid siphoned off will equal the displacement fluid by the strut.

Figure 3:
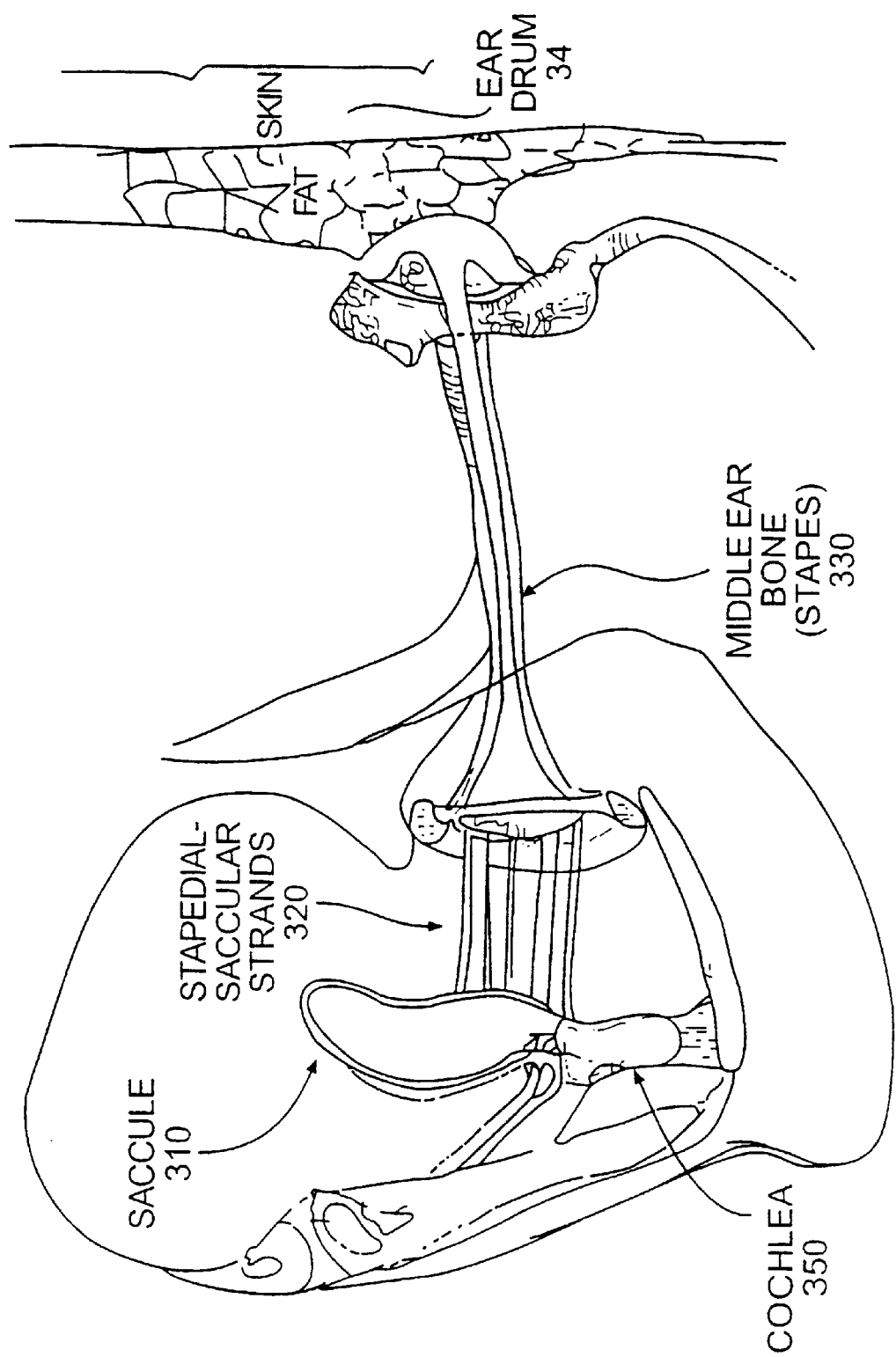
FIG. 3 is a diagram of a dissected marine turtle middle ear showing the natural fibroelastic strands that connect the saccule to the stapes.

The appearance of the struts in the human ear will be similar to that in the turtle model shown in FIG. 3. The number of struts implanted for the human ear will typically be far less than the number of fibroelastic strands 320 in the turtle inner ear that connect the turtle saccule 310 to the turtle stapes 330, but the mechanical results will be similar.

Figure 4:
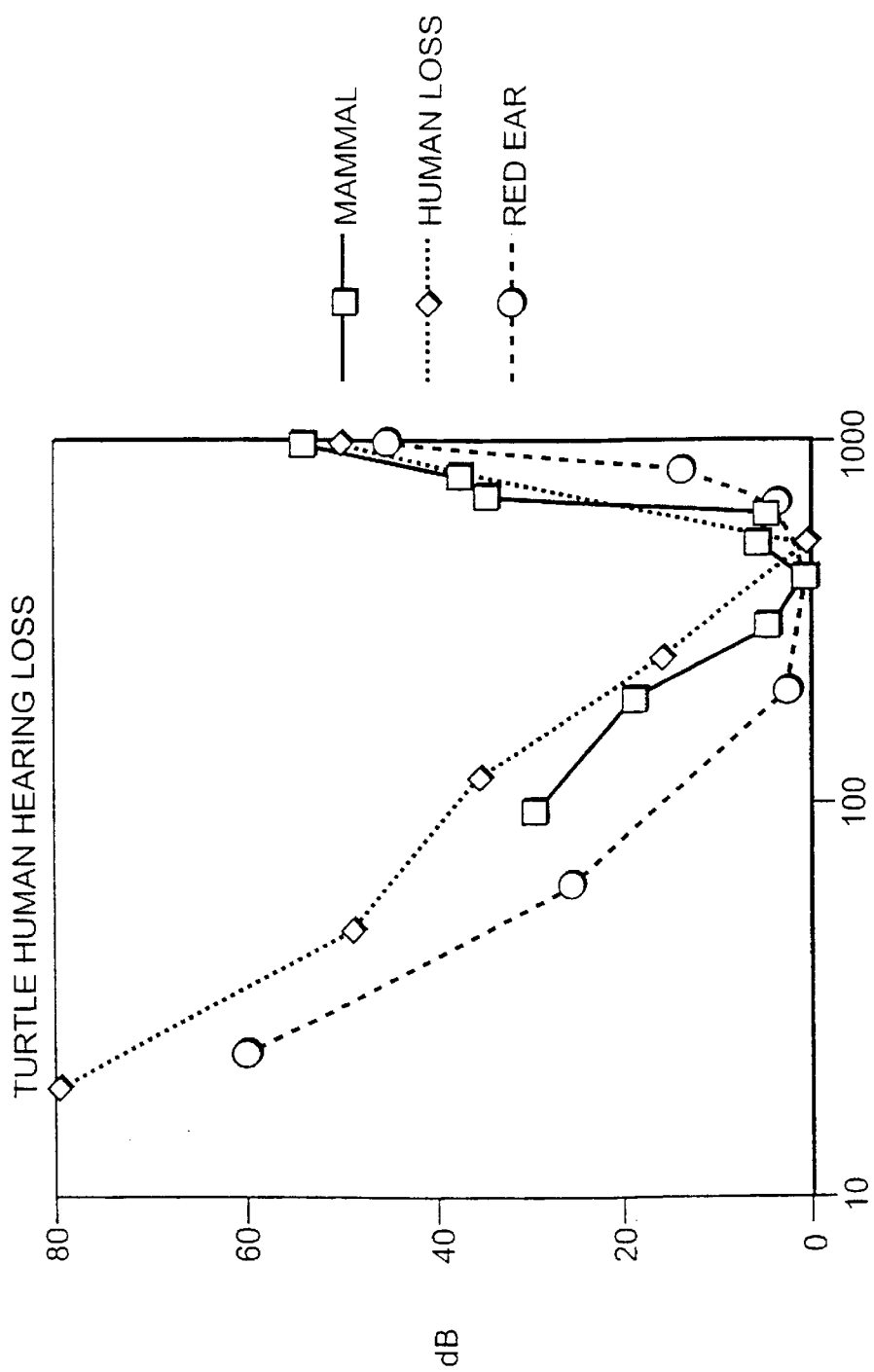
FIG. 4 shows comparison audiograms of a human with a severe loss of hearing above 1000 Hz (human loss), of a red ear turtle, and a typical tuning curve of an auditory fiber in the apex of a mammalian cochlea (mammal)

The turtle (red ear slider) audiogram is shown in FIG. 4. The turtle ear is not very sensitive to frequencies about 1000 Hz. A human with little hearing above 1000 Hz reveals a similar relative (sensation level re: best frequency hearing) audiometric plot, as also shown in FIG. 4. Additionally, the nerve fibers in the apex of a mammalian cochlea that are broadly tuned in the low frequencies also share the same basic audiometric configuration, as also shown in FIG. 4. As can be seen from these audiograms, the human with a severe hearing loss above 1000 Hz, the turtle and the auditory fiber from the apex of the cochlea share quite similar frequency characteristics. That is, hard of hearing humans, with intact apical portions of their cochleas, have a similar auditory sensitivity in frequency range to turtles. The plots in FIG. 4 are in dB sensation level (SL), which is determined by arbitrarily setting the most sensitive frequency as a reference frequency and by referencing other frequency points to that reference frequency.

If there are few receptor (hair) cells remaining in a damaged human cochlea, amplification in the high frequencies for an air-conduction type of hearing aid will have little benefit, while high level amplification in the low frequencies will not be well tolerated. With increasing low frequency loss, the only alternative for air-conduction type of hearing aids is to increase the level of amplification. The present invention, however, offers an alternative to the use of amplification alone.

For a patient having a damaged cochlea, when the saccule is coupled to the middle ear by the use of the implanted struts, both the damaged cochlea and the saccule are stimulated simultaneously by the sound coming into the ear. The saccule auditory fibers are tuned much like that of the auditory fibers of the base of the cochlea.

Figure 5:
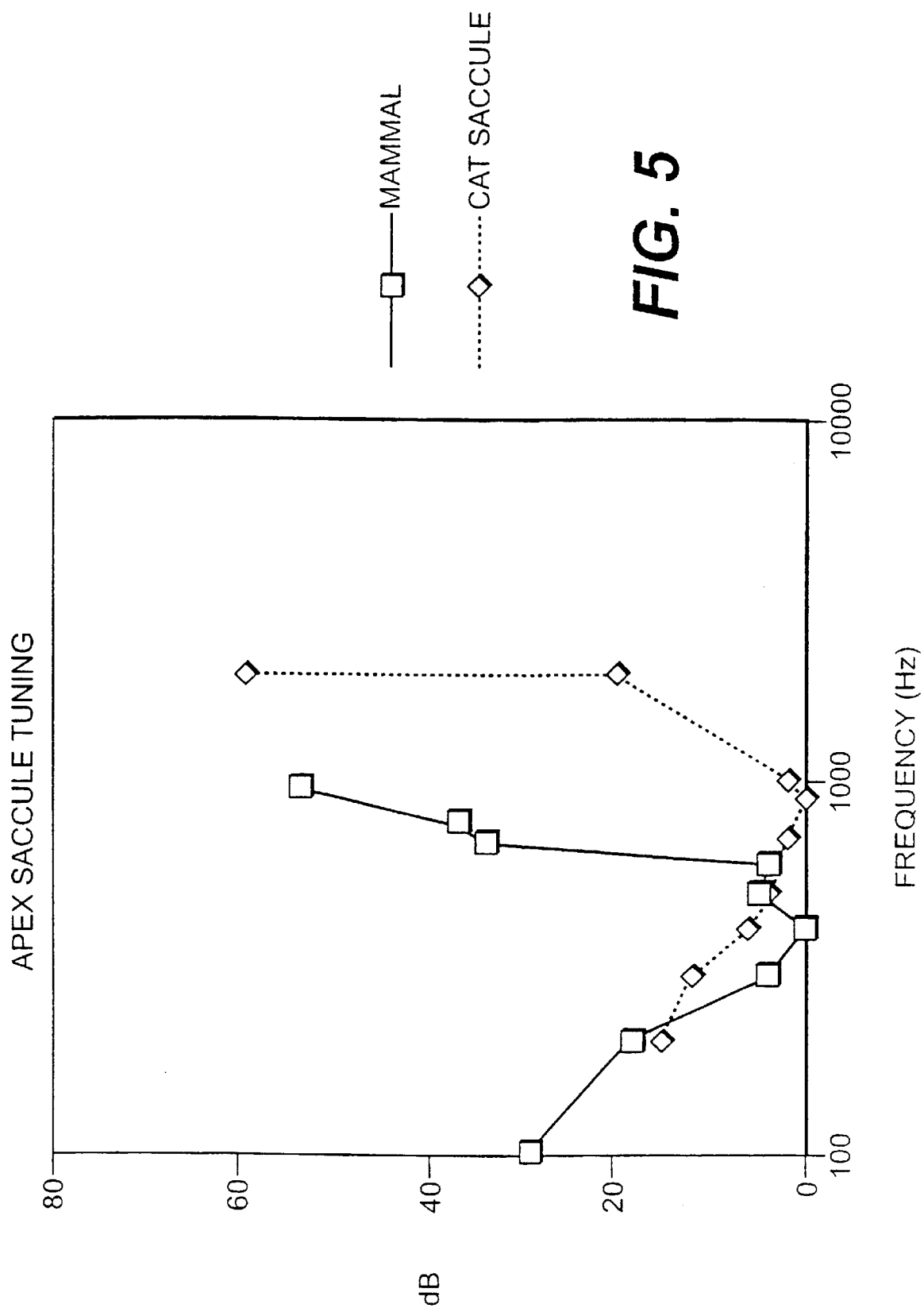
FIG. 5 shows a similarity between an auditory nerve fiber in the apex of a cat cochlea and a saccular nerve fiber in the cat that responds to sound.
Figure 6A:
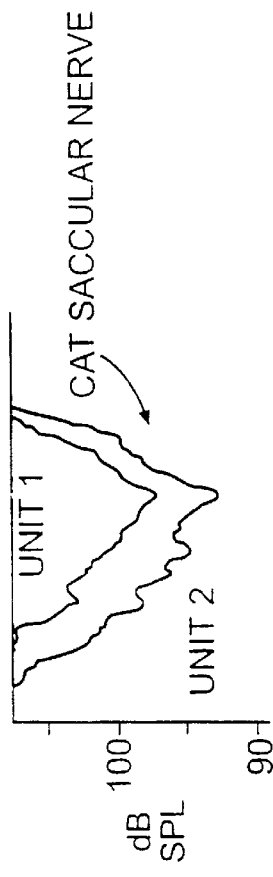
FIG. 6A shows the actual saccular nerve response to two fibers in the cat.
Figure 6B:
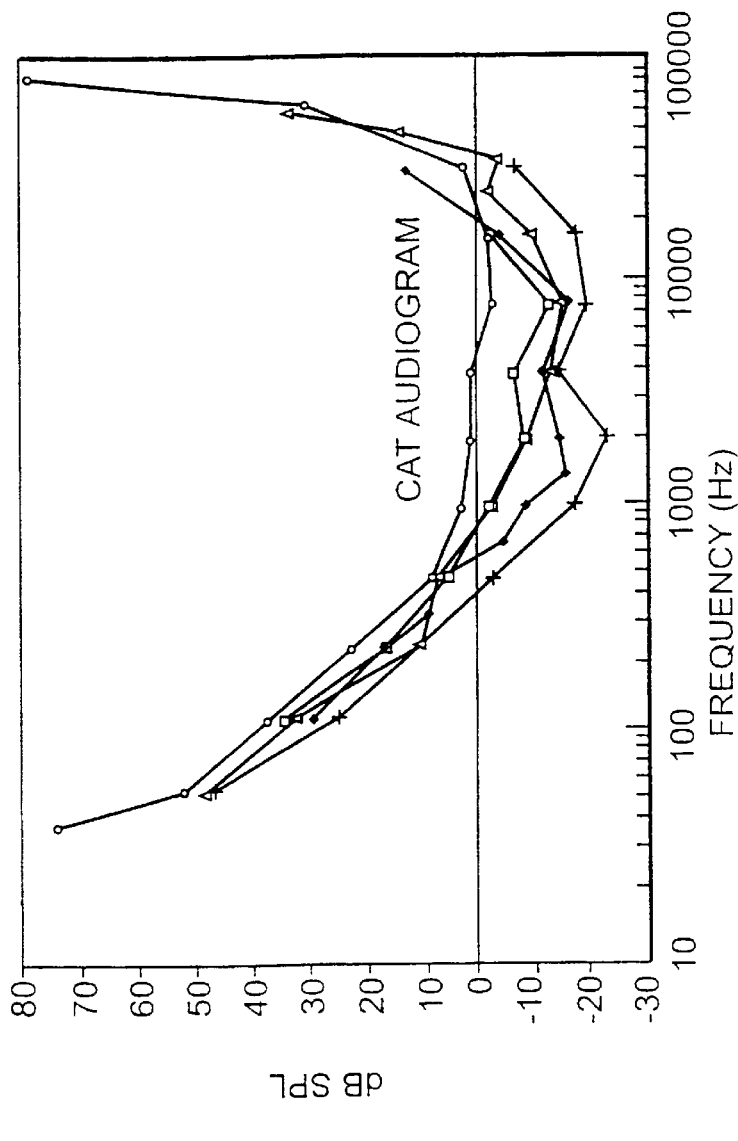
FIG. 6B shows a typical cat audiogram.

The fibers of the saccule have a similar shape based on the data available, which is shown in FIG. 5. FIG. 5 provides a comparison of the frequency response of an auditory nerve fiber in the apex of a mammalian cochlea with that of a saccular nerve fiber that responds to sound in a cat. Referring now to FIGS. 6A and 6B, for a cat saccule, some saccule fibers can be stimulated naturally by sound if it is intense (95 dB SPL, which is 115 dB above threshold, 115 dB SL). Note that the saccular fibers do not begin to fire until the sound level is 115 dB SL. The threshold of the saccular fiber at 1000 Hz is about 95 dB SPL and the audiogram of a cat at 1000 Hz is about −20 dB SPL. The data plotted in FIGS. 6A and 6B was obtained from various articles on audiograms of a cat: Costalupes (1983); Elliot, Stein and Harrison (1960); Heffner and Heffner (1985); Neff and Hind (1955); Miller and Covel (1963).

If the saccule was connected to the stapes, such as by using one or more struts in accordance with the present invention, the threshold of the saccular fibers would be much lower due to the direct transmission of vibration to the saccule. The struts according to the embodiments of the present invention provide the direct transmission path.

The basic phenomenon of saccular hearing for mammals has been known, and the details of cat saccular hearing is described in an article entitled "Acoustic Responses From Primary Afferent Neurons Of The Mammalian Sacculus", by M. P. McCue & J. J. Guinan, Jr., published in "Mass. Eye & Ear Infirmary", Boston, Mass., 1993. However, since the saccule is not coupled to the eardrum's displacement in the human ear, the sound power has to be of sufficient strength to move the head before the saccule is stimulated. Not until the present invention has there been an approach to take useful advantage of the saccule for hearing.

Figure 7:
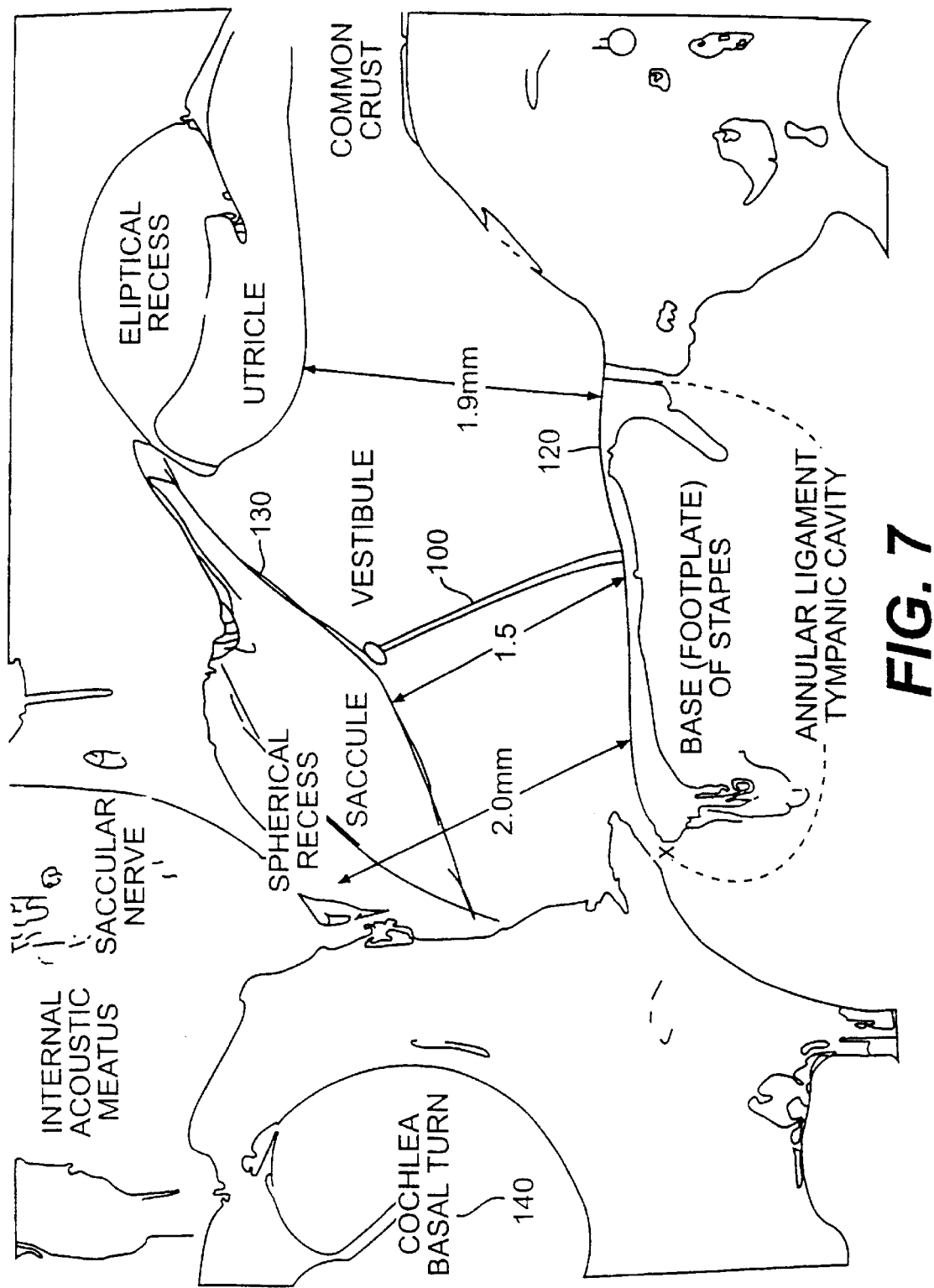
FIG. 7 shows the spatial relation between the footplate of the stapes and the saccular wall for a human inner ear.

The implantation struts according to the embodiments of the present invention connect the footplate of the stapes to the saccular wall. The anatomy of the area of the inner ear where the struts are to be implanted is shown in FIG. 7A. Strut 100 is placed in the 1.5 mm area (vestibule) between the saccule 130 and the base (footplate) of the stapes 120, and connect at respective ends to these elements. The strut 100 is preferaby about 1.6 mm in length, to allow for the strut to provide some pressure on the saccular wall, with a small portion (e.g., slightly less than 0.1 mm) of the strut 100 being inserted into a hole drilled into the stapes 120.

Figure 8A:
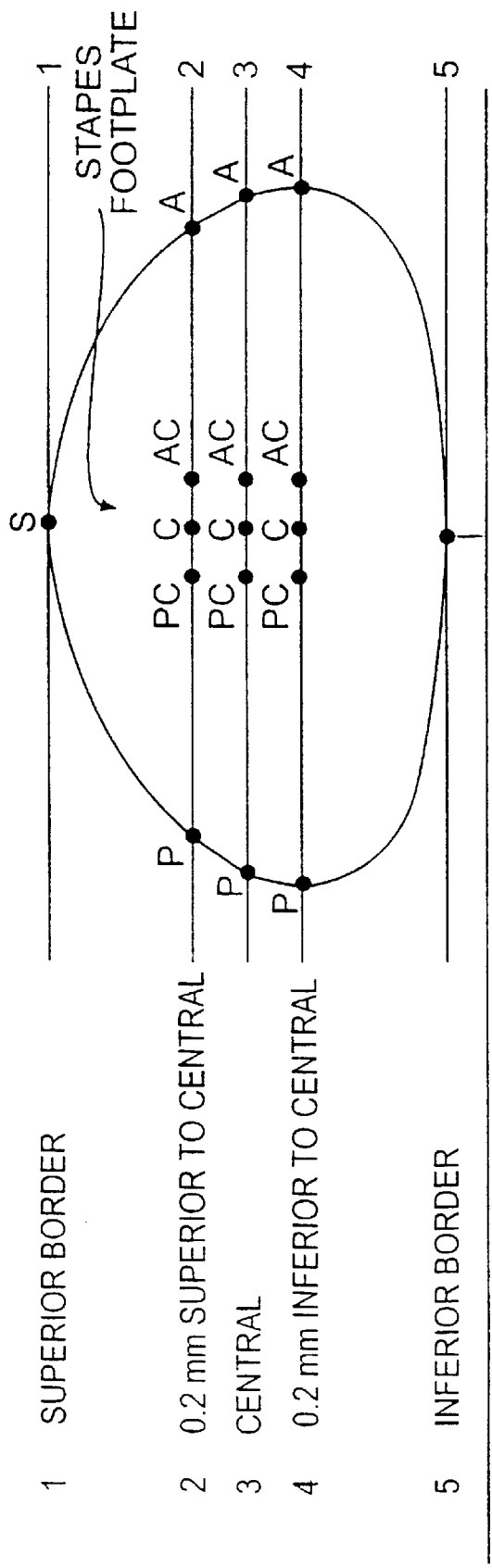

FIGS. 8A and 8B show data values and a corresponding plot of the distance between the saccule and the stapes, based on data obtained from an article by Pauw et al., entitled "Utricle, Saccule & Cochlear Duct in Relation to Stapedotomy", published in "Ann. Otol. Rhinol. Laryngology", page 967, in 1991. For the embodiments of the present invention, an insertion distance of 1.6 mm is chosen as a base value to ensure safety. Of course, the exact size of the struts may vary depending upon the particular inner ear characteristics of a patient. As explained above, each of the struts is inserted about 1.6 mm into a hole drilled near the center of the footplate of the stapes. This provides a connection of one end of the struts to the stapes, while the other end is free. In one embodiment, the connection of that other end of the struts to the saccule is made by inflating a reservoir end of the sleeve with uncured, liquid sylastic, which then cures to thereby provide a "fluid spring" connection of that end of the strut to the saccular wall. In another embodiment, a pushing of the sleeve (used to create the strut) away from the saccule cause a balloon-like formation of uncured sylastic (pumped into the hollow middle of the sleeve) to form, and to cure in that shape.

As discussed above, the system and method according to the embodiments of the present invention activate the saccular receptors with eardrum displacements, with those eardrum displacements being provided to the saccule via struts connecting the stapes (that moves based on movements of the eardrum) to the saccular wall. Sound entering the ear canal and activating the middle ear is capable of stimulating of endorgans, the saccule and the cochlea, when the strut is positioned between the footplate of the stapes and the saccular wall. In particular, each of the embodiments of the present invention is well-suited for persons with severe high-frequency sensorineural hearing loss.

It has been found that the saccule is sensitive to sound when the cochlear contribution is eliminated by ototoxic poisoning. The threshold of the saccular response is about 70 dB above normal cochlear sensitivity, in a normal human ear. This higher threshold exists because the head must be set to vibration by the sound to activate saccular receptors. However, when a strut or struts are disposed between the footplate of the stapes and the saccule in accordance with the present invention, the saccule is mass loaded with the middle ear structures, and becomes stimulated at a lower threshold level.

In certain embodiments of the present invention, a stapedial-saccular strut is positioned by first drilling a hole near the center of the footplate of the stapes. A sleeve, formed from already-cured sylastic and having a cylindrical shape with a hollow middle, is inserted into the hole drilled in the footplate. In particular, the footplate of the stapes is drilled until the bone is thin and transparent. As soon as the drilling has been performed to form the hole, the sleeve is inserted into the drilled hole. Care must be taken of course in the drilling procedure, since the stapes footplate is embedded in the oval window, and if the oval window is punctured, perilymph will escape, which may cause deafness. When the footplate is drilled to a point that it almost becomes transparent, the sleeve is immediately inserted. At this point, a drill bit may be inserted into the sleeve while the hole is only partially drilled, so that the exact depth of the hole can be accomplished with care by using the sleeve itself to achieve the desired size. In any event, the sleeve must be inserted quickly, the perilymph loss minimized, and the sylastic injected into the sleeve to thereby form the strut. Since the sleeve is hollow and made of cured sylastic, there is flexibility to seal the hole at the footplate and maneuverability before the injected liquid sylastic (into the hollow portion of the sleeve) begins to cure. The curing time is a function of the solvent mix making up the liquid sylastic, and may be modified somewhat based on experimentation as to the time needed to perform a strut insertion. In the case of a persistent leak, the sleeve itself may have to remain within the inner ear, and as long as the sleeve is moved off of the saccular wall, this is acceptable. Basically, it is important in this procedure that the hole in the stapes be sealed quickly, and that the correct amount of perilymph is siphoned off (based on displacement caused by introduction of a prothesis in the inner ear. Other types of insertion techniques to implant the strut into the footplate may be contemplated by those skilled in the art while remaining within the scope of the invention as described herein. The sealing of the hole is performed by the injecting of uncured sylastic into the hollow end of the sleeve nearest the stapes, whereby the uncured sylastic forms around the drilled hole to provide a rigid connection of the strut to the stapes when the strut cures to achieve a solid form.

As discussed above, after the sleeve has been attached to the stapes, liquid silicon (e.g., sylastic) is injected into the sleeve. In the first embodiment of the invention, when the liquid silicon is injected into the sleeve, the reservoir end of the sleeve expands. The expanded end of the strut comes in contact with the saccular wall and adheres thereto. In the second embodiment of the invention that does not use a sleeve having a reservoir end, pulling of the sleeve in a direction away from the saccule causes a balloon-like formation of uncured sylastic to form at the end of the strut closest to the saccule. This balloon end provides a contact point to the saccular wall. The injecting of the uncured liquid sylastic into the hollow middle of the sleeve may be performed, for example, by placing a syringe needle at the bottom of the sleeve, then injecting the liquid sylastic from the syringe to the hollow middle of the sleeve, and then slowly withdrawing the syringe. In the preferred embodiments, the sylastic is slowly injected and the sleeve is slow removed. In this way, the needle is generally positioned near the medial end of the sleeve. In cases where the sleeve cannot be removed fully, the amount extending into the footplate is trimmed, and sealed with sylastic. Multiple struts may be used, but care must be taken to remove the quantity of perilymph displaced by the insertion of each strut into the footplate of the stapes.

In the embodiments of the invention, it is preferable that the angular ligament as well as the stapedius muscle remain intact during the strut insertion process. The angular ligament keeps the stapes from too much displacement (limits the maximum displacement), which is important so that the strut is not pushed too much against the saccule when it is put in place.

As explained above, the sleeve (made out of cured sylastic) forms a template for injecting uncured, liquid sylastic into the ear. Then, as the uncured sylastic starts to cure and achieve a solid form, the sleeve is removed from the inner ear. The sleeve is preferably removed since it may cause a problem with loud noise exposure, which may cause vibrations translated from the footplate to the saccular wall (by way of the strut) that may rupture the saccule. Once the sleeve is removed, the remaining cured sylastic that was pumped into the hollow middle portion of the sleeve remains, thereby forming a strut or prosthesis that provides a vibration bridge between the footplate of the stapes and the saccular wall. If, however, it is not possible to remove the sleeve during formation of the strut, then it can be left inside the inner ear, and care must be take such that the patient is not exposed to very loud noises. In these cases, a sylastic sponge may be utilized, which can be inserted into the stapes and sealed with sylastic. The sponge would provide some protection from strong stapes displacement due to loud sound stimulation. The sponge would also keep its shape, and would also adhere to the saccular wall in time.

In the embodiments of the present invention, it is important to choose a strut having the correct length to fit into the space between the stapes and the saccular for a particular person. This length may be obtained by performing an MRI of the person's ear, to thereby determine that distance. As explained above, the struts are made out of biomaterials, such as biocompatible silicon, such that the strut is not extruded. Furthermore, the strut is designed so that it maintains adequate contact with the saccular wall. That end of the strut may be provided with a suitable adhesive in order to provide a reliable contact with the saccular wall. In particular, due to the injecting of uncured sylastic into a sleeve to thereby form a prothesis inside the inner ear, the sylastic balloon end of the prothesis is in contact with the saccular wall, and adhesions will naturally occur to keep it in place over time. Note that the sylastic will attach to the medial end of the strut and will cure fastest at the stapes end since it is exposed to air, and can even be "air dried", if necessary. This air curing of the strut at the stapes end will seal the hole that was drilled into the footplate of the stapes when the strut was formed between the stapes and the saccule.

Referring now to FIG. 9A, in the first embodiment of the present invention, the sleeve 900 is hollow with an expandable balloon reservoir end 110, with that end 110 shown in the unexpanded state. The reservoir end 110 is capable of expanding when the sleeve 900 is injected with a silicon material, to thereby form a structure with an expanded end 110, as shown in FIG. 9B. The expanded (balloon) end 110 of the sleeve 900 makes contact with the saccular wall, and adheres thereto. The balloon is preferably constructed of a biocompatible elastic material, to ensure adequate contact with the saccular wall. In the second embodiment of the present invention, the sleeve is formed without a reservoir end, and just has a hollow, cylindrical shape. The balloon end is formed by pushing the sleeve in a direction away from the saccule, after the sleeve has been positioned between the saccule and the stapes and after uncured, liquid sylastic has been injected into the hollow middle of the sleeve to thereby form the strut.

While preferred embodiments have been described herein, modification of the described embodiments may become apparent to those of ordinary skill in the art, following the teachings of the invention, without departing from the scope of the invention as set forth in the appended claims. For example, while strut was described in one embodiment as being constructed from a biocompatible organic polymer, such as sylastic, other types of biocompatible organic polymers, such as a water well hydrophilic gel or the like, may be used instead. Also, while details of a strut constructed according to one embodiment have been provided, one of ordinary skill in the art will recognize that other types of strut constructions may be envisioned to provide a prosthesis between the stapes and the saccule, while remaining within the spirit and scope of the invention as described herein.

For example, as an alternative to using a sleeve to provide a structure for curing a strut inside an ear, a sylastic element can be cast outside of the ear into a desired shape, and then the cured sylastic element can be inserted into a hole drilled in the footplate of the stapes, so as to provide connectivity between the stapes and the saccule. Using this alternative, the end of the strut inserted into the hole drilled in the footplate of the stapes will not immediately bond to the stapes, but adhesions will eventually form to provide for a rigid connection of the stapes and the strut.

The particular shape of the strut formed between the stapes and the saccule is described in detail, but other shapes may be envisioned. The primary purpose of the strut is to provide a "vibration bridge" between these two elements, and a strut may be configured with any particular shape that achieves this translation of vibrations in the footplate of the stapes to resultant vibrations to the saccular wall.

Additionally, the extra mass of the stapes caused by the strut attached thereto may lower the frequency response of the user, which may result in additional high frequency hearing loss. However, since the invention has been developed for persons who already have high frequency hearing loss, this extra high frequency hearing loss is not that important. On the contrary, the mass loading of the stapes may, in fact, increase low frequency sensitivity, which is very beneficial to the user.

What is claimed is:

1. An auditory prosthesis system adapted to be inserted into a human ear having a saccule and a stapes, the auditory prosthesis system comprising:

at least one strut that is adapted to be disposed between the saccule and the stapes, wherein movement of the stapes is directed to the saccule by way of the at least one strut, wherein a first end of the strut is adapted to be connected to the stapes, and wherein a second end of the strut is adapted to be non-rigidly connected to the saccule.

2. The auditory prosthesis system according to claim 1, wherein the hollow middle of the sleeve includes a silicon material in an uncured form, and the expandable balloon reservoir is adapted to extend from the second end of the sleeve due to the silicon material, thereby contacting with the saccule, and wherein the silicon material in an uncured form eventually cures to form the strut.

3. The auditory prosthesis system according to claim 1, wherein the strut is an elastic member and has a conical shape.

4. A method of implanting a hearing aid device into an ear of a human, the inner ear including a saccule and a stapes, the method comprising:

a) positioning a first end of a sleeve to the stapes, wherein the sleeve has a hollow middle for receiving a biocompatible material in an uncured form, the sleeve having a second end provided adjacent to the saccule; and b) applying the biocompatible material in the uncured form into the hollow middle of the sleeve, wherein a strut is formed when the biocompatible material cures, wherein a first end of the strut is coupled to the stapes and a second end of the strut is coupled to the saccule and wherein movement of the stapes is directed to the saccule by way of the strut.

5. The method according to claim 4, wherein the movement of the stapes is caused in part by movement of an eardrum of the ear.

6. The method according to claim 4, wherein a plurality of said struts are implanted into the ear by performing the steps a) and b) repeatedly.

7. The method according to claim 4, wherein a first end of the strut is rigidly connected to the stapes, and a second end of the strut is non-rigidly connected to the saccule.

8. The method according to claim 4, wherein the second end of the sleeve includes an expandable balloon reservoir.

9. The method according to claim 8, wherein, when the hollow middle of the sleeve is filled with the biocompatible material in an uncured form, the expandable balloon reservoir extends from the second end of the sleeve, thereby forming the strut having a balloon end that contacts the saccule.

10. The method according to claim 4, wherein the strut is an elastic chamber and has a conical shape.

11. The method according to claim 4, wherein the strut is made from a biocompatible organic polymer.

12. The method according to claim 4, wherein the biocompatible material is a biocompatible organic polymer made from sylastic and a water swell hydrophilic gel.

13. The method according to claim 4, wherein the stapes includes a footplate, and wherein the first end of the strut is affixed to a central portion of the footplate.

14. The method according to claim 4, further comprising the step of:

removing the sleeve while the biocompatible material is curing to form the strut having a shape similar to that of the sleeve.

15. A method of implanting a prosthesis into an ear to enhance hearing, the method comprising the steps of:

a) providing a strut between a saccule and a stapes of the ear, thereby providing a direct contact between the saccule and the stapes, wherein the strut provides direct stimulation of the saccule based on stimulation of the stapes.

16. The method according to claim 15, wherein the strut provides a mass load to the stapes, to thereby increase a low frequency sensitivity of the ear.

* * * * *